(12) United States Patent
Taniguchi et al.

(10) Patent No.: US 10,823,792 B2
(45) Date of Patent: Nov. 3, 2020

(54) MAGNETIC RESONANCE IMAGING DEVICE, MAGNETIC RESONANCE IMAGING SYSTEM, AND PARAMETER ESTIMATION METHOD

(71) Applicant: Hitachi, Ltd., Tokyo (JP)

(72) Inventors: Yo Taniguchi, Tokyo (JP); Tomoki Amemiya, Tokyo (JP); Suguru Yokosawa, Tokyo (JP); Toru Shirai, Tokyo (JP); Hisaaki Ochi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 18 days.

(21) Appl. No.: 16/233,154

(22) Filed: Dec. 27, 2018

(65) Prior Publication Data

US 2019/0227134 A1 Jul. 25, 2019

(30) Foreign Application Priority Data

Jan. 24, 2018 (JP) .................................. 2018-009813

(51) Int. Cl.
| | |
|---|---|
| *G01R 33/36* | (2006.01) |
| *G01R 33/56* | (2006.01) |
| *G01R 33/385* | (2006.01) |
| *G06T 11/00* | (2006.01) |
| *A61B 5/055* | (2006.01) |

(Continued)

(52) U.S. Cl.
CPC .......... *G01R 33/3607* (2013.01); *A61B 5/055* (2013.01); *G01R 33/385* (2013.01); *G01R 33/4831* (2013.01); *G01R 33/4833* (2013.01); *G01R 33/50* (2013.01); *G01R 33/5608* (2013.01); *G06T 11/006* (2013.01); *G06T 11/008* (2013.01); *G06T 2207/10088* (2013.01)

(58) Field of Classification Search
CPC ............ G01R 33/3607; G01R 33/4833; G01R 33/50; G01R 33/4831; G01R 33/385; G01R 33/5608; G01R 33/56; G01R 33/4806; G06T 11/006; G06T 11/008; G06T 2207/10088; A61B 5/055
USPC ......................................... 324/318; 600/410
See application file for complete search history.

(56) References Cited

U.S. PATENT DOCUMENTS

2015/0338492 A1* 11/2015 Sato ....................... G01R 33/50
600/410

FOREIGN PATENT DOCUMENTS

JP 2011-024926 A 2/2011

OTHER PUBLICATIONS

Dennis Atkinson, et al., Improved MR Angiography: Magnetization Transfer Suppression with Variable Flip Angle Excitation and Increased Resolution, Radiology Mar. 1994, 190:890-894.

* cited by examiner

*Primary Examiner* — Farhana A Hoque
(74) *Attorney, Agent, or Firm* — Mattingly & Malur, PC

(57) ABSTRACT

In a case where a subject parameter distribution is obtained using MRI, a magnetization transfer effect is suppressed such that the calculation accuracy of T1 and T2 of brain parenchyma can be improved and a variation in the T1 value of blood caused by the effect of blood flow can be reduced. In imaging for parameter estimation, a magnetization transfer effect is suppressed by using a high frequency magnetic field pulse having a narrow frequency band as an excitation pulse. In a case where the frequency band is narrow, the high frequency magnetic field pulse has a shape in which the (Continued)

excitation profile is similar to a Gaussian function. A rising portion of the shape is arranged in a field of view where the head is an imaging target.

12 Claims, 16 Drawing Sheets

(51) Int. Cl.
*G01R 33/483* (2006.01)
*G01R 33/50* (2006.01)

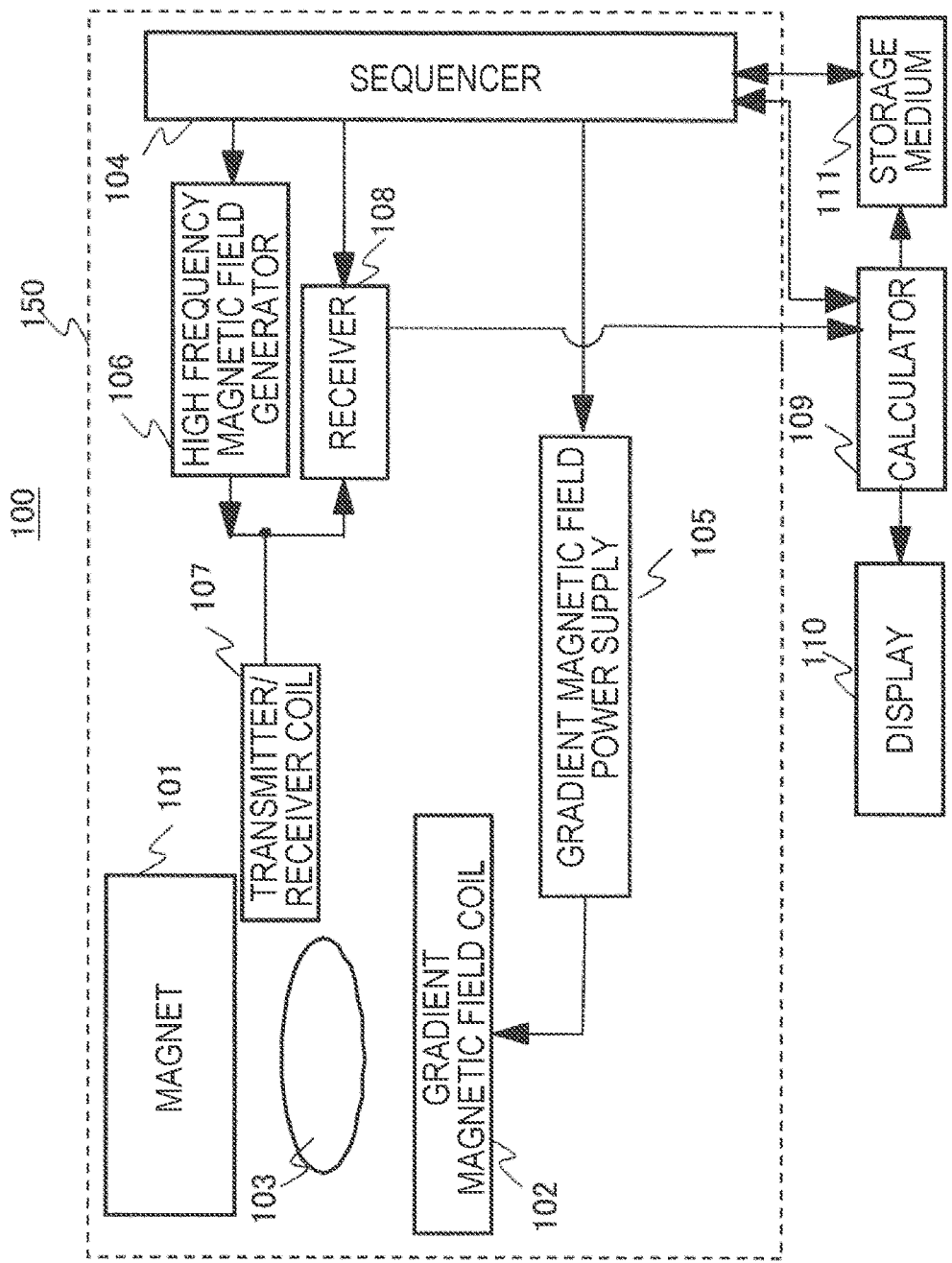
[FIG. 1]

[FIG. 2]
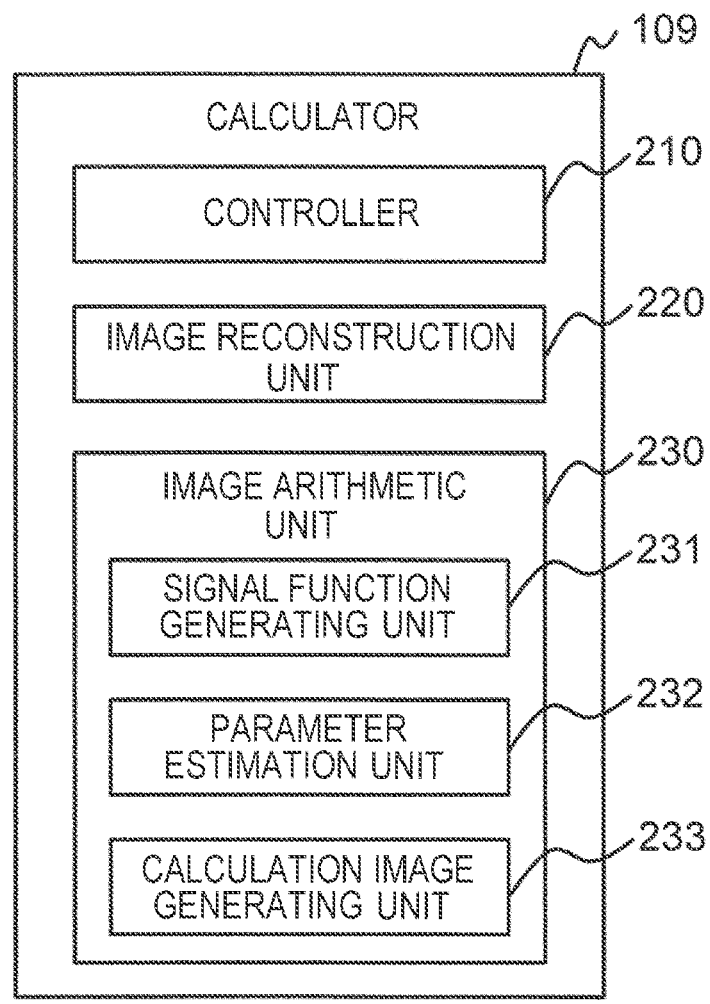

[FIG. 3]
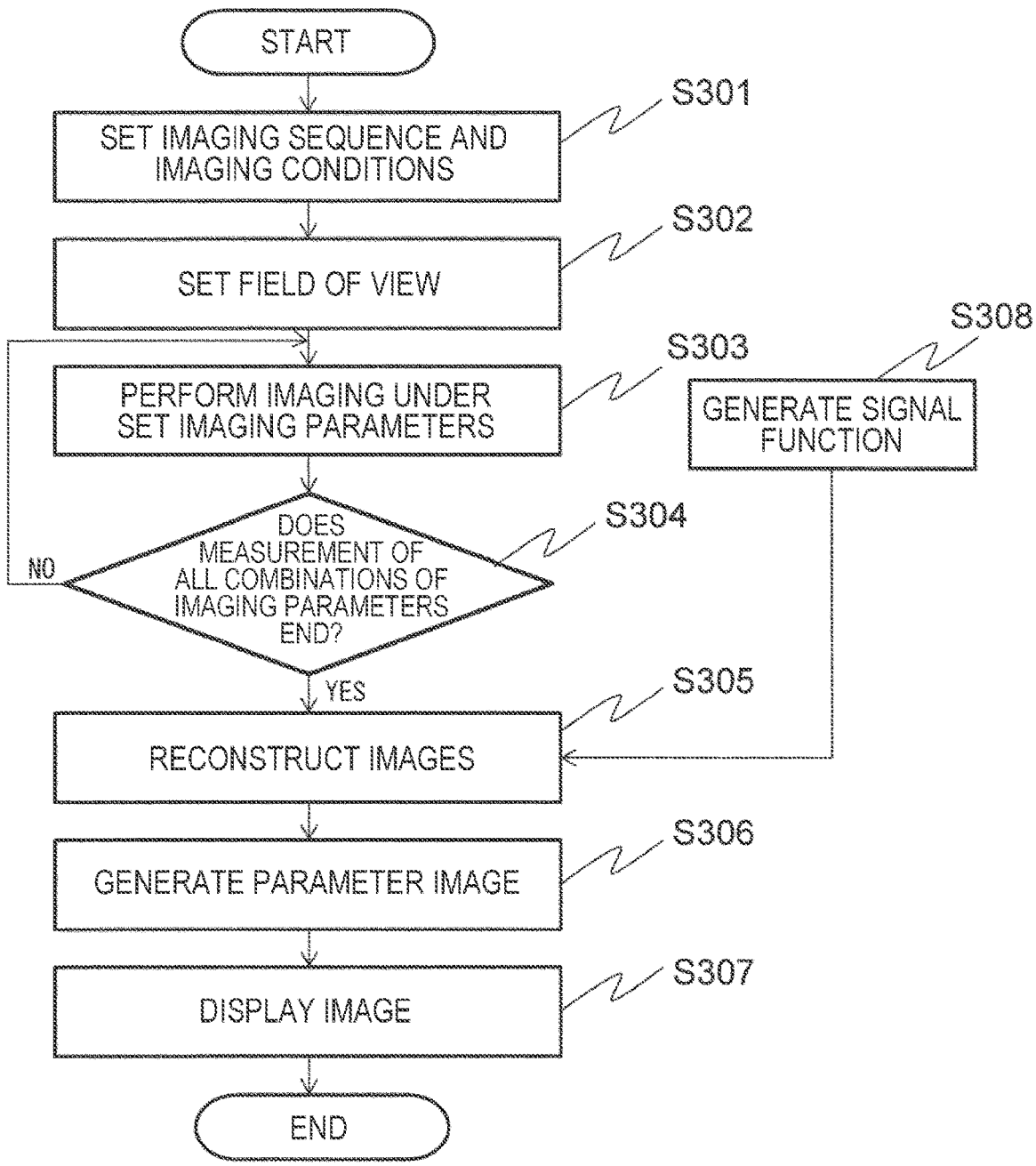

[FIG. 4]
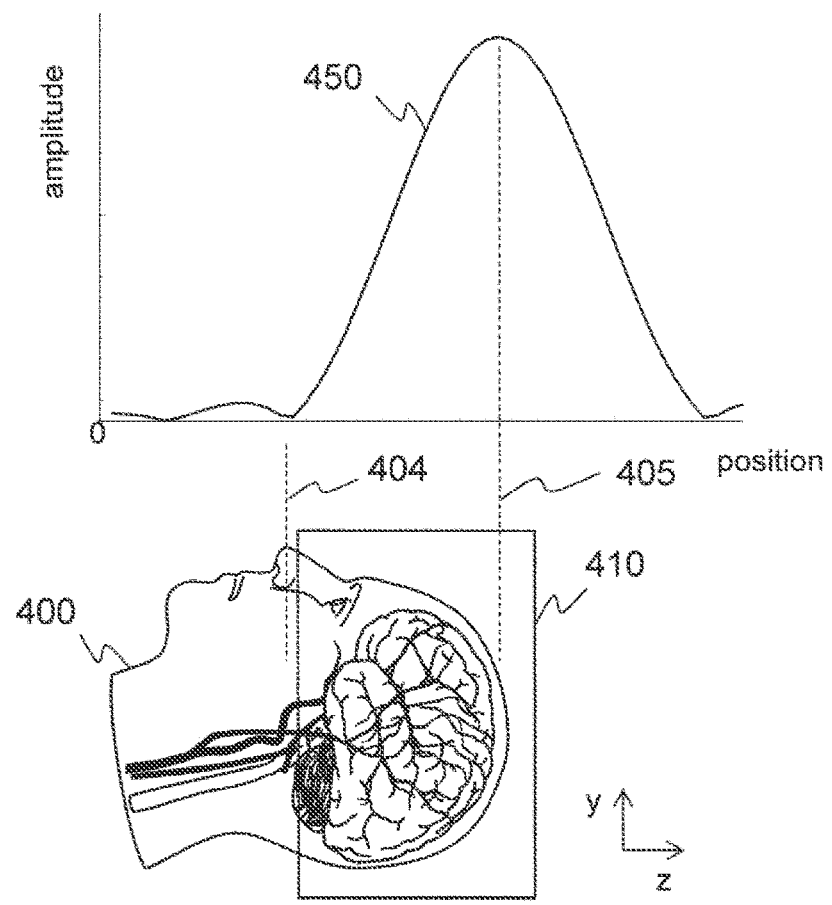

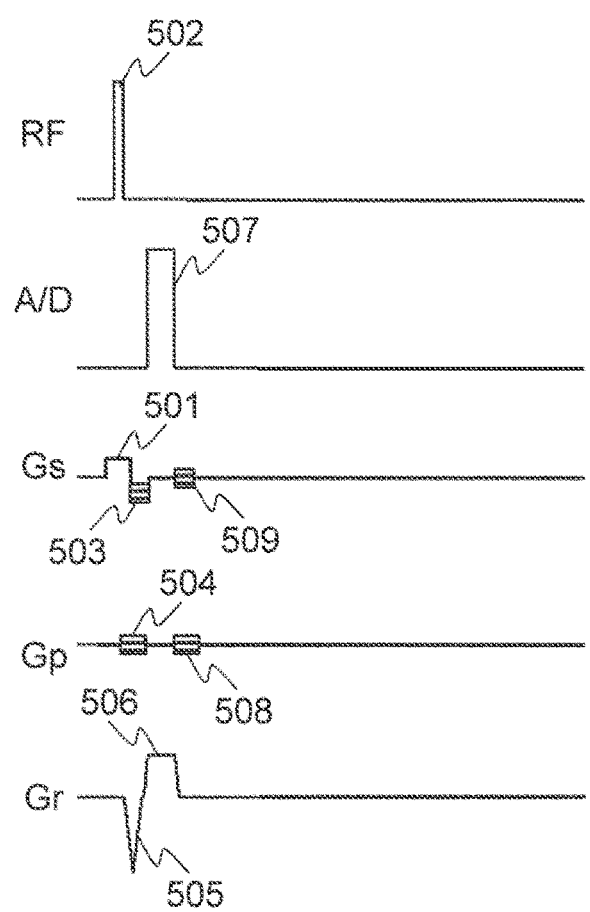
[FIG. 5]

[FIG. 6]
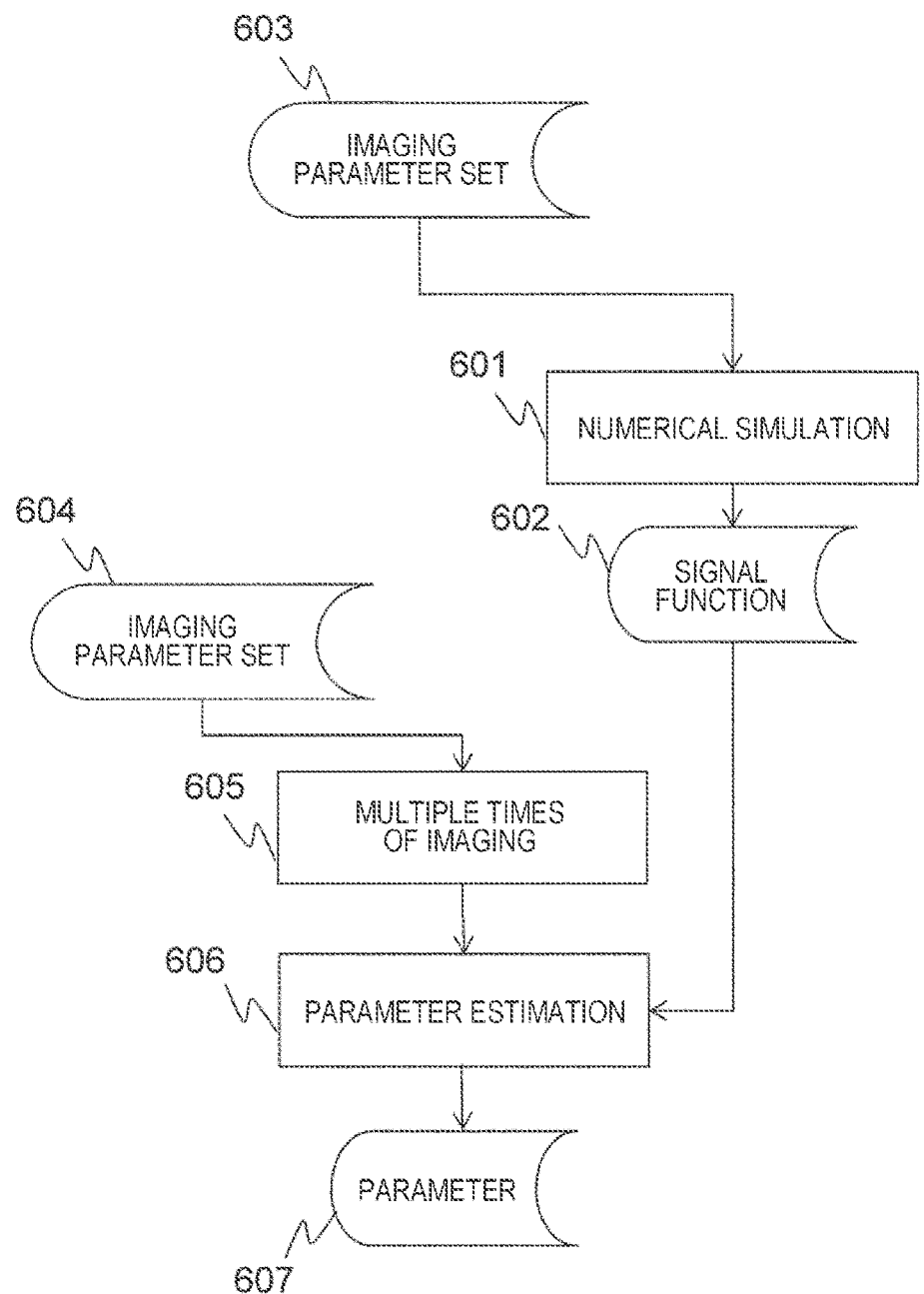

[FIG. 7]
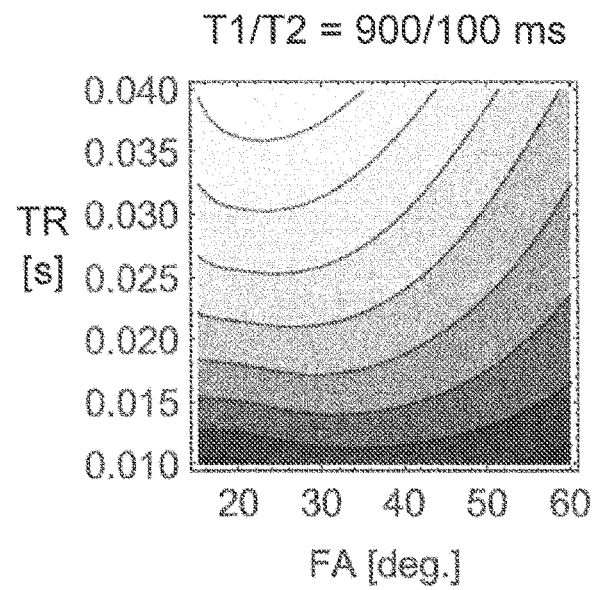
[FIG. 8]
| P | FA (DEG.) | Θ (DEG.) | TR (MIN.) |
|---|---|---|---|
| 1 | 10 | 8 | 0.03 |
| 2 | 40 | 2 | 0.01 |
| 3 | 40 | 2 | 0.04 |
| 4 | 40 | 5 | 0.01 |
| 5 | 40 | 7 | 0.01 |
| 6 | 40 | 22 | 0.03 |

[FIG. 9A]
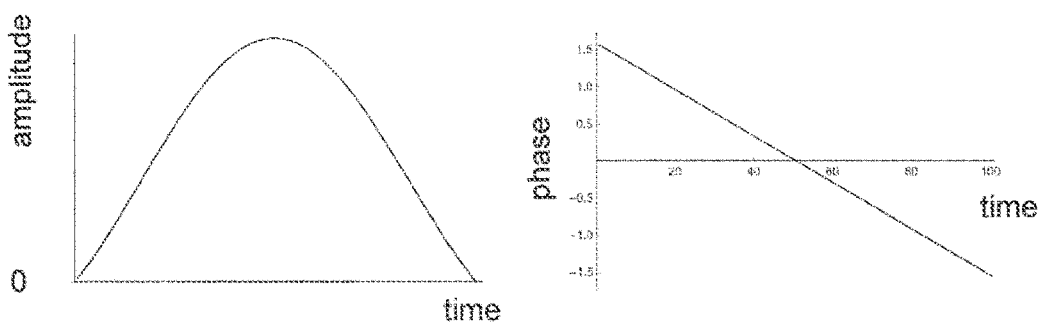
[FIG. 9B]
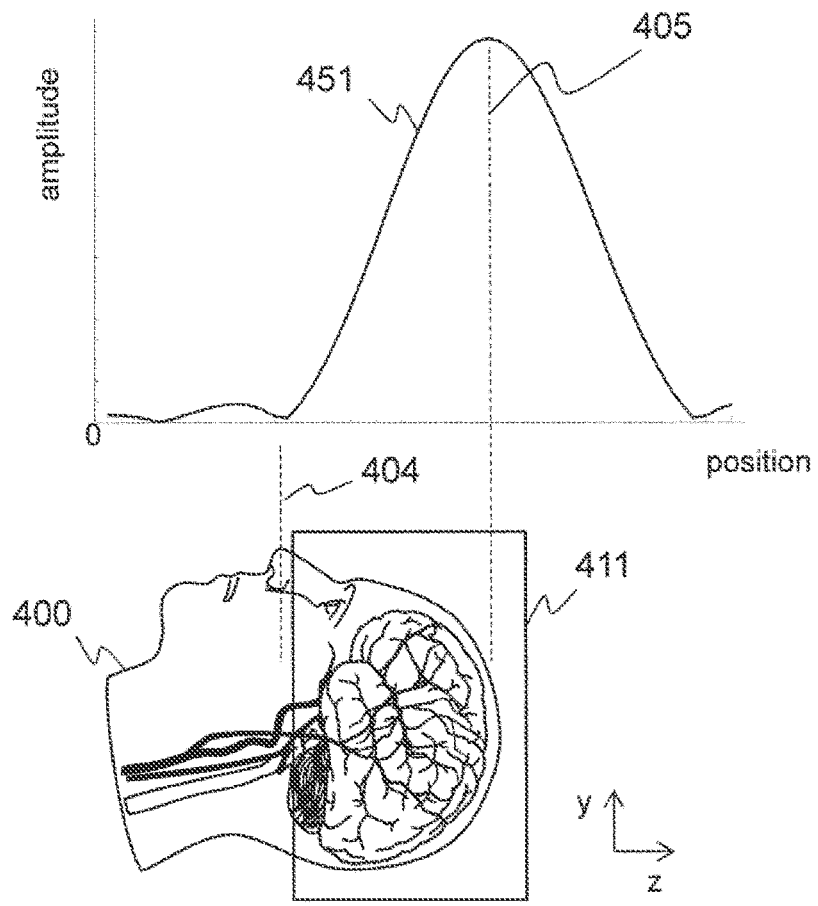

[FIG. 10]

| band width [kHz] | T1 of white matter |
|---|---|
| 0.84 | 889 ms |
| 2.5 | 1.5 s |
| 5.6 | 1.7 s |

[FIG. 11A]
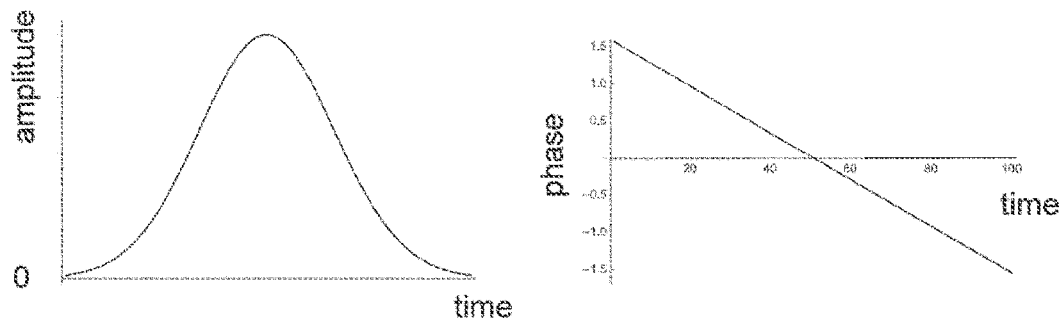
[FIG. 11B]
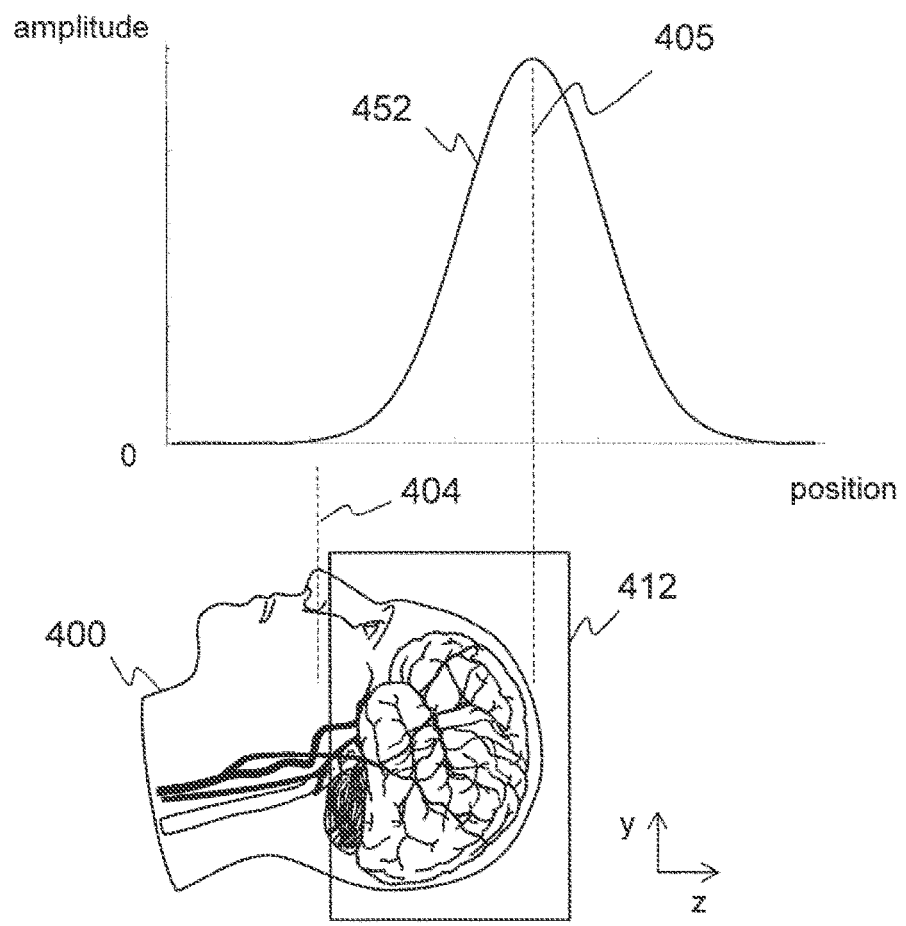

[FIG. 12A]
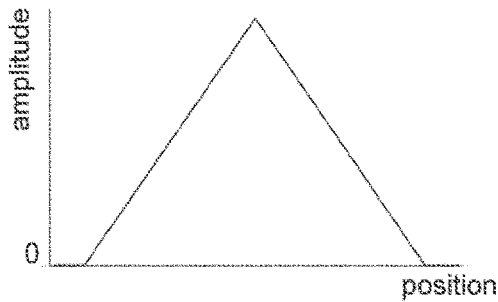
[FIG. 12B]
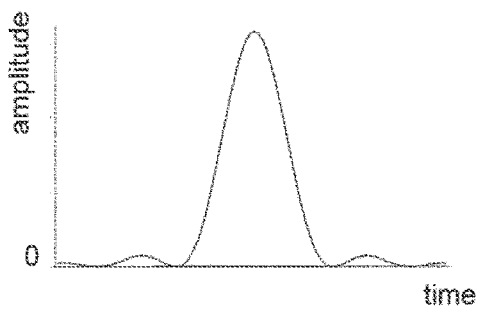
[FIG. 12C]
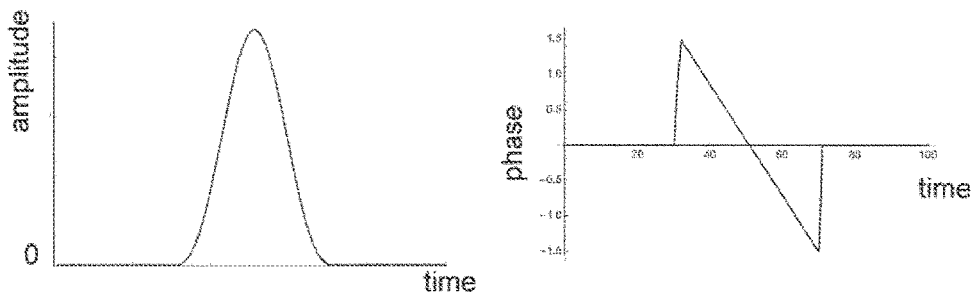
[FIG. 12D]
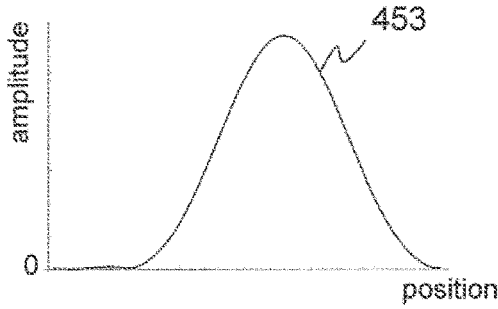

[FIG. 13]
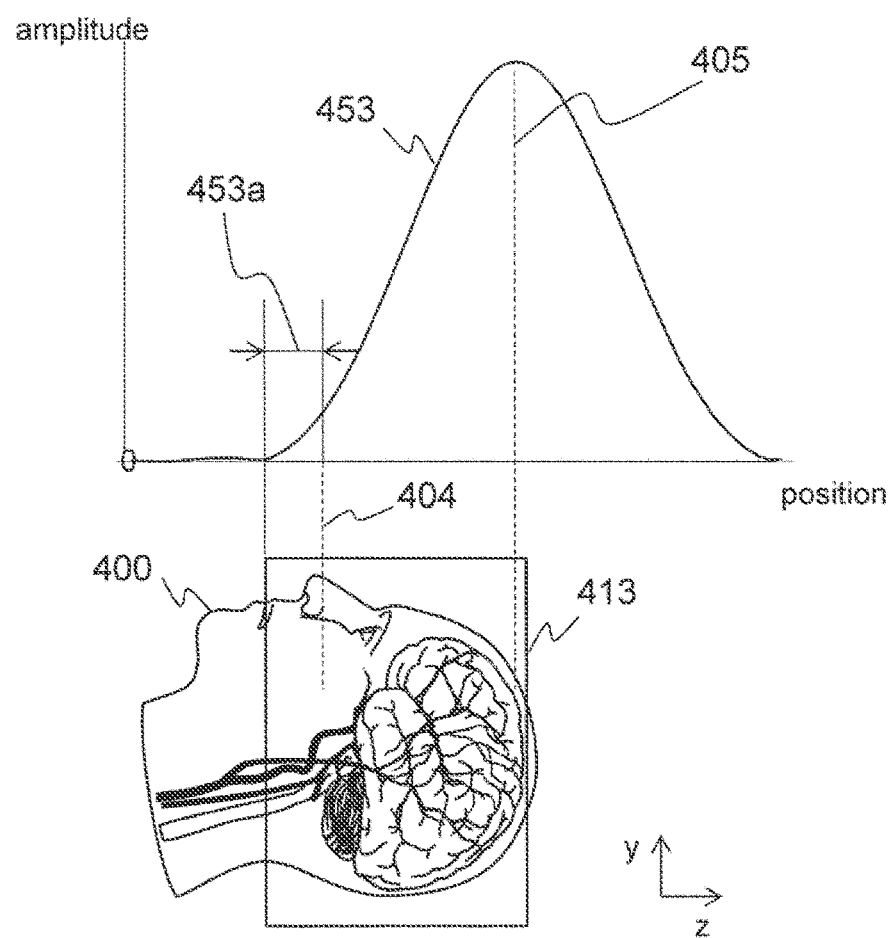

[FIG. 14A] 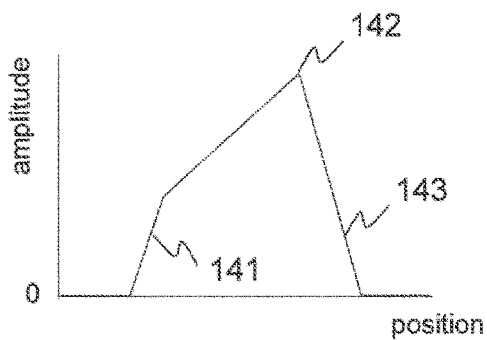
[FIG. 14B] 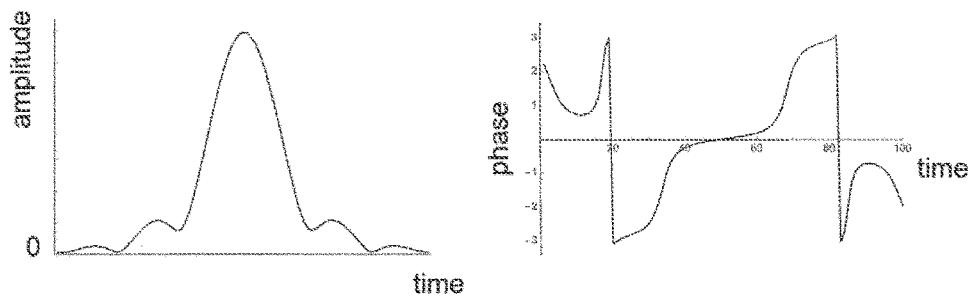
[FIG. 14C] 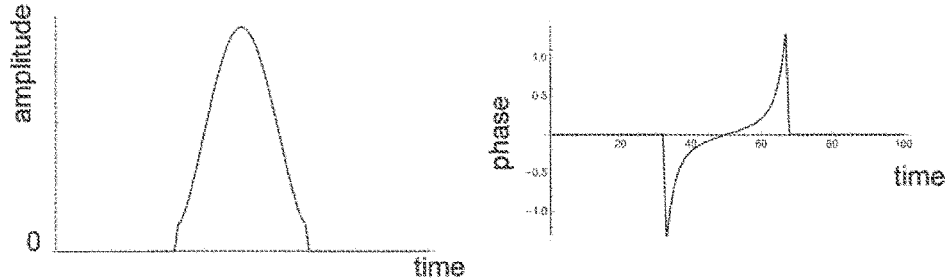
[FIG. 14D] 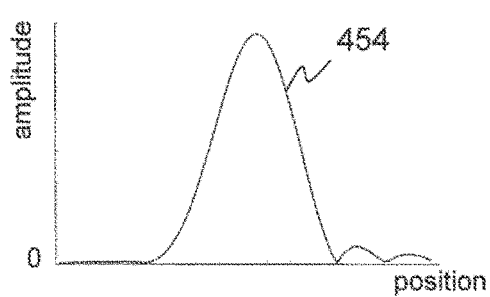

[FIG. 15]
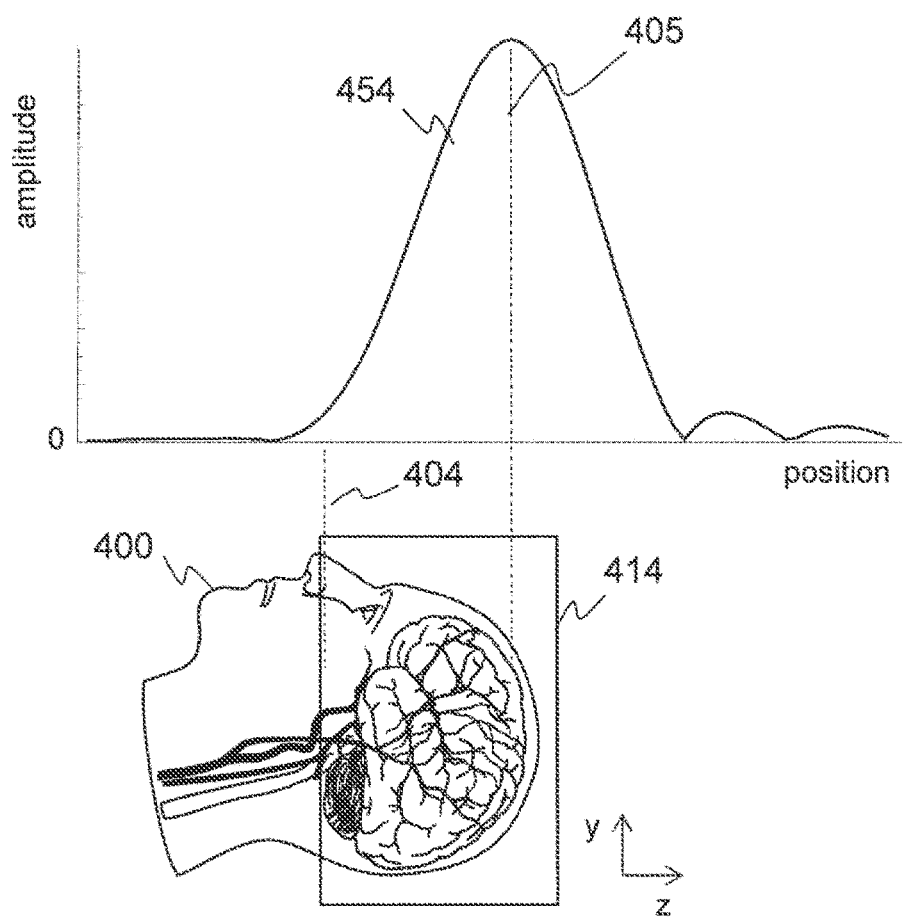

[FIG. 16A]
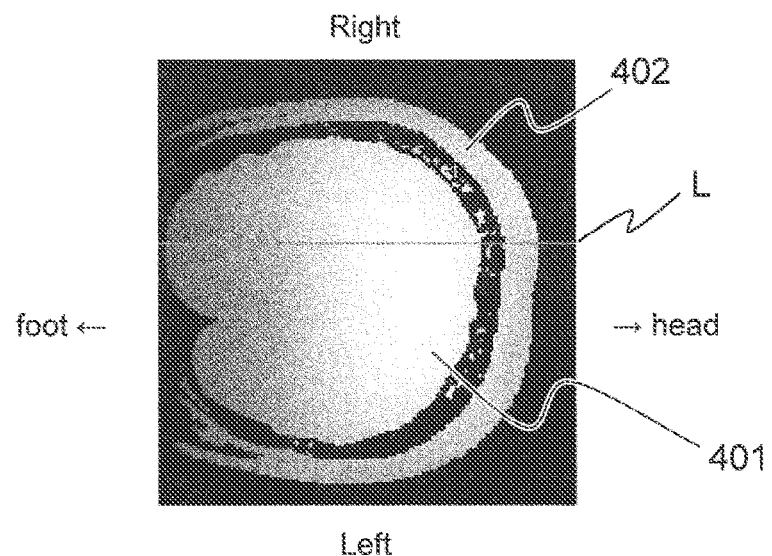
[FIG. 16B]
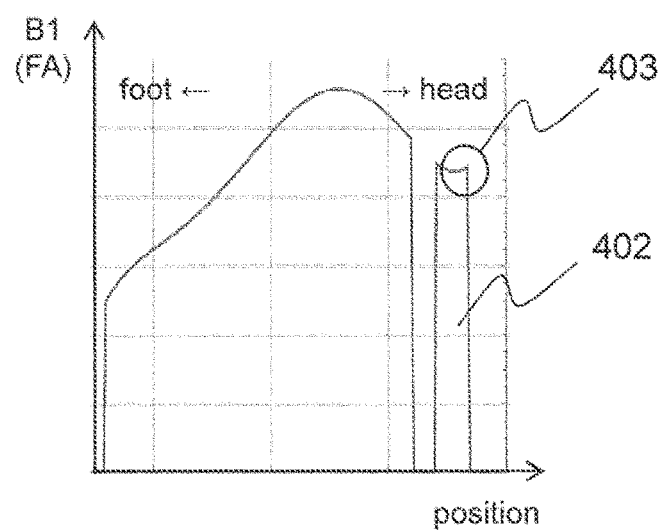

[FIG. 17]
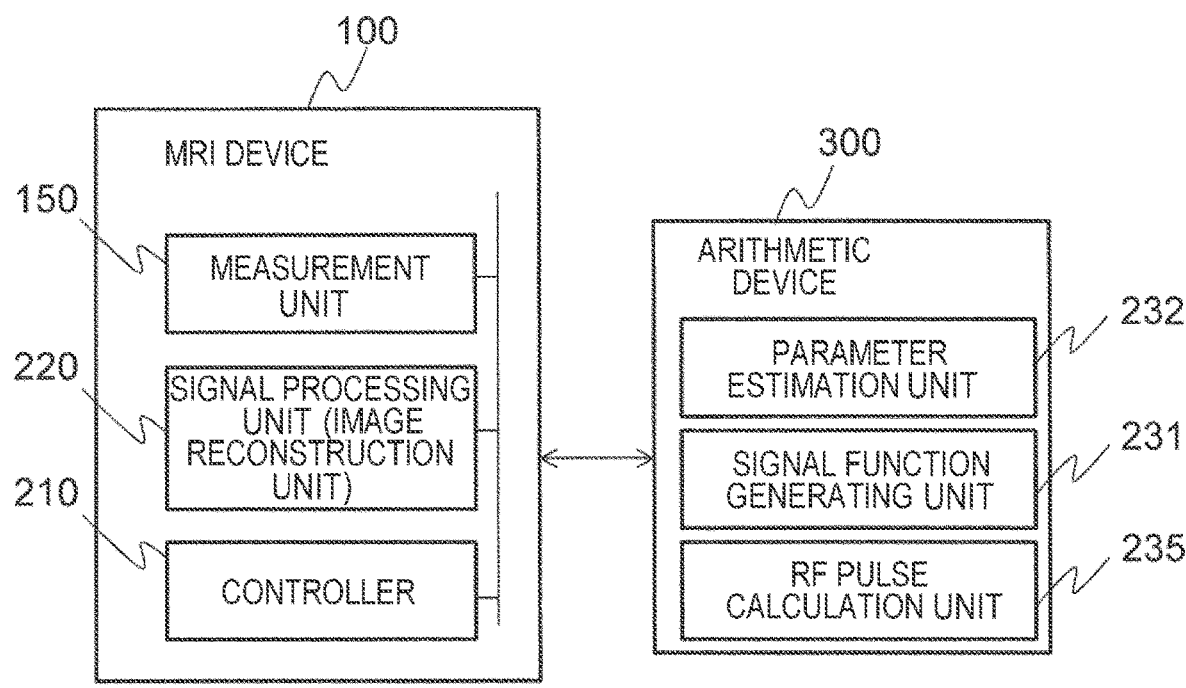

MAGNETIC RESONANCE IMAGING DEVICE, MAGNETIC RESONANCE IMAGING SYSTEM, AND PARAMETER ESTIMATION METHOD

CROSS-REFERENCE TO RELATED APPLICATION

The present application claims priority from Japanese application JP 2018-009813, filed on Jan. 24, 2018, the contents of which is hereby incorporated by reference into this application.

TECHNICAL FIELD

The present invention relates to a magnetic resonance imaging device and, in particular, relates to a technique of estimating a subject parameter by calculation.

BACKGROUND ART

A magnetic resonance imaging (MRI) device a medical image diagnostic device that obtains an image of a subject by causing nuclear magnetic resonance to occur in specific nuclei included in a tissue of a subject, typically, in hydrogen nuclei, receiving a nuclear magnetic resonance signal (echo signal) generated by the nuclear magnetic resonance, and reconstructing an image based on the received nuclear magnetic resonance signal.

The intensity of the nuclear magnetic resonance signal obtained from the MRI device largely depends on the spin density of hydrogen nuclei in a tissue, and also varies depending on device conditions, imaging conditions such as a pulse sequence used for imaging or imaging parameters, and subject side factors such as characteristics of a subject tissue. The device conditions include magnetic field intensity and a receiving sensitivity distribution, which are collectively referred to as "device parameters". In addition, the imaging parameters include a repetition time, a set intensity of a high frequency magnetic field, and a phase of a high frequency magnetic field. The subject side factors include not only the spin density but also a longitudinal relaxation time, a transverse relaxation time, a resonance frequency, a diffusion coefficient, and an irradiation intensity distribution of a high frequency magnetic field, which are collectively referred to as "subject parameters".

There is disclosed a method in which, among plural parameters that determine the intensity of the nuclear magnetic resonance signal, a value of a specific parameter is obtained by inter-image calculation using a signal function that represents a relationship between the parameter value and the signal intensity such that the parameter value is set as a pixel value (PTL 1). An image obtained from this method is called, for example, a calculated image or a quantitative value image.

Once a pulse sequence is determined, a signal function can be analytically obtained. However, PTL 1 discloses the method in which a signal function is obtained even from an imaging pulse sequence, which is not analytically obtained, by numerical simulation to generate a calculated image. Specifically, PTL 1 discloses an example in which a signal function is obtained from, for example, RF-spoiled GE, which is a GE (Gradient Echo) fast imaging sequence, to estimate a parameter such as a relaxation time, an irradiation intensity of a high frequency magnetic field, or a proton density.

On the other hand, one MRI imaging method is MR angiography in which only blood flow is imaged. In a case where a range having a given volume such as the head is imaged, blood flow moves in this volume, and thus there is a problem in that the signal intensity changes. NPL 1 discloses that, in MR angiography of the head, a blood vessel in a field of view is uniformly imaged using an excitation pulse (referred to as "gradient excitation pulse") in which a flip angle (intensity) of a high frequency magnetic field pulse that excites spinning gradually increases from the neck to the vertex of the head.

CITATION LIST

Patent Literature

PTL 1: JP-A-2011-024926

Non-Patent Literature

NPL 1: Atkinson D, et al., Improved MR Angiography: Magnetization Transfer Suppression with Variable Flip Angle Excitation and Increased Resolution, Radiology 1994, 190:890-894.

SUMMARY OF INVENTION

Technical Problem

In order to obtain a calculated image, it is necessary that imaging is performed multiple times using different imaging parameters. In the technique disclosed in PTL 1, the GE fast imaging sequence is used in order to reduce the imaging time required to obtain a calculated image. In this imaging sequence, it is necessary that a high frequency magnetic field pulse is continuously irradiated within a short repetition time.

Due to this reason, there is a problem in that a subject parameter of blood is not uniform depending on regions of a three-dimensional calculated image of the head. Specifically, during imaging of the calculated image, blood flows from the neck into an imaging region and then flows in a vertex direction. During this time, the blood is continuously excited by irradiation of a high frequency magnetic field pulse, the blood becomes saturated as it flows to the vertex, and the signal decreases. In general, as the longitudinal relaxation time (T1 value) increases, the signal tends to decrease. Accordingly, in a case where the T1 value is calculated based on a measured signal value, the calculated T1 value of the blood increases as the blood flows to the vertex.

In order to solve this problem, the use of the gradient excitation pulse disclosed in NPL 1 is considered. By using the gradient excitation pulse, the signal of blood is uniform without depending on regions. However, the gradient excitation pulse has a wide frequency band, and thus has a high magnetization transfer effect. Therefore, in a case where the gradient excitation pulse is used to obtain a calculated image for imaging, there is a problem in that the accuracy of the T1 value of brain parenchyma decreases. That is, in a case where the gradient excitation pulse is continuously irradiated within a short repetition time, protein in brain parenchyma having a short transverse relaxation time (T2) is widely excited, and protons coupled to the protein are saturated. Therefore, the signal of water decreases along with magnetization transfer between protein and water, and the calculated T1 value of brain parenchyma tends to be long.

The present invention has been made in consideration of the above-described circumstances, and an object thereof is to provide a technique of obtaining a calculated value image in which a T1 value of blood can be made to be uniform by preventing the calculation accuracy of T1 and T2 of brain parenchyma from deteriorating due to a magnetization transfer effect and suppressing an effect of blood flow.

Solution to Problem

In order to achieve the object, the present invention suppresses the magnetization transfer effect by using a high frequency magnetic field pulse having a narrow frequency band in an imaging sequence for obtaining a calculated value image. The high frequency magnetic field pulse having a narrow frequency band has a shape in which the excitation profile is similar to a Gaussian function. Therefore, a rising portion of the shape is arranged in, for example, a field of view where the head is an imaging target to implement a gradient excitation state.

Specifically, according to the present invention, there is provided an MRI device including: a measurement unit that applies a high frequency magnetic field and a gradient magnetic field to a subject placed in a static magnetic field according to a predetermined imaging sequence to measure an echo signal generated from the subject; an image reconstruction unit that obtains a reconstructed image from the measured echo signal; and a parameter estimation unit that estimates a quantitative value distribution of the subject using a plurality of reconstructed images and a signal function, the reconstructed images being obtained by performing imaging multiple times under different imaging conditions of the imaging sequence, and the signal function determining a relationship between a quantitative value of the subject and a signal value of each of the reconstructed images. The measurement unit uses, as a high frequency magnetic field pulse for excitation to be used in the imaging sequence, a high frequency magnetic field pulse that has a peak in the vicinity of one end portion of a field of view and provides an excitation profile having a shape in which the excitation profile decreases substantially symmetrically on opposite sides of the peak. The high frequency magnetic field pulse has a narrow frequency band of, for example, 1 kHz or lower.

Advantageous Effects of Invention

According to the present invention, in imaging for obtaining a calculated image, a high frequency magnetic field pulse having a narrow frequency band that provides an excitation profile in which the excitation profile increases monotonously from one end to another end of the field of view is used. As a result, a signal of blood can be prevented from being attenuated from one end to another end of the field of view. Therefore, a change in T1 value depending on blood flow can be prevented, and a uniform T1 value can be calculated. In addition, by using the excitation pulse having a narrow frequency band, the magnetization transfer effect can be reduced. Therefore, the accuracy of T1 and T2 of brain parenchyma in a calculated image does not deteriorate.

BRIEF DESCRIPTION OF DRAWINGS

FIG. 1 is a diagram illustrating a schematic overall configuration of an MRI device to which the present invention is applied.

FIG. 2 is a functional block diagram of a calculator.

FIG. 3 is a flowchart illustrating the procedure of imaging.

FIG. 4 is a diagram illustrating a relationship between an excitation profile and a field of view.

FIG. 5 is a diagram illustrating an example of a pulse sequence used for imaging.

FIG. 6 is a diagram illustrating the procedure of parameter estimation.

FIG. 7 is a diagram illustrating a part of an intensity of a signal function.

FIG. 8 is a diagram illustrating an example of parameter sets used for parameter estimation.

FIG. 9A is a diagram illustrating a waveform and a phase of a RF pulse according to Example 1, and FIG. 9B is a diagram illustrating a positional relationship between an excitation profile of the RF pulse and a field of view.

FIG. 10 is a diagram illustrating a relationship between a frequency band of the RF pulse and a brain white matter T1 value.

FIG. 11A is a diagram illustrating a waveform and a phase of a RF pulse according to Example 2, and FIG. 11B is a diagram illustrating a positional relationship between an excitation profile of the RF pulse and a field of view.

FIGS. 12A-12D are diagrams illustrating a method of designing a RF pulse according to Example 3, in which FIG. 12A illustrates a designated excitation profile, FIG. 12B illustrates a waveform obtained by Fourier-transformation of the waveform of FIG. 12A, FIG. 12C illustrates a waveform obtained by removing side lobes from the waveform of FIG. 12B and a phase, and FIG. 12D is a diagram illustrating a waveform obtained by inverse Fourier-transformation of the waveform of FIG. 12C.

FIG. 13 is a diagram illustrating a positional relationship between the waveform (excitation profile) of FIG. 12D and a field of view.

FIGS. 14A-14D are diagrams illustrating a method of designing a RF pulse according to Example 4, in which FIG. 14A illustrates a designated excitation profile, FIG. 14B illustrates a waveform obtained by Fourier-transformation of the waveform of FIG. 14A and a phase, FIG. 14C illustrates a waveform obtained by removing side lobes from the waveform of FIG. 14B and a phase, and FIG. 14D is a diagram illustrating a waveform obtained by inverse Fourier-transformation of the waveform of FIG. 14C.

FIG. 15 is a diagram illustrating a positional relationship between the excitation profile of Example 4 and a field of view.

FIG. 16A is an imaged image, and FIG. 16B is a diagram illustrating a B1 distribution in a line L of FIG. 16A.

FIG. 17 is a diagram illustrating a magnetic resonance imaging system.

DESCRIPTION OF EMBODIMENTS

First Embodiment

Hereinafter, a first embodiment to which the present invention is applied will be described. Hereinafter, in all the diagrams for describing the embodiment of the present invention, components having the same functions are represented by the same reference numerals, and the description thereof will not be repeated.

First, an overall configuration of an MRI device according to the embodiment will be described. FIG. 1 is a block diagram illustrating a schematic configuration of an MRI device 100 according to the embodiment. The MRI device 100 includes: a magnet 101 that generates a static magnetic field; a gradient magnetic field coil 102 that generates a gradient magnetic field; a sequencer 104; a gradient magnetic field power supply 105; a high frequency magnetic field generator 106; a transmitter/receiver coil 107 that irradiates a high frequency magnetic field and detects a nuclear magnetic resonance signal; a receiver 108; a calculator 109; a display 110; and a storage medium 111. Hereinafter, the respective elements other than the calculator 109, the display 110, and the storage medium 111 will be collectively referred to as "measurement unit 150". In the drawing, the transmitter/receiver coil 107 is illustrated as a single element. However, a transmitter coil and a receiver coil may be separately provided.

A subject (for example, a biological body) 103 is arranged on a bed (table) in a static magnetic field space that is generated by the magnet 101. In addition, the sequencer 104 instructs the gradient magnetic field power supply 105 and the high frequency magnetic field generator 106 to generate a gradient magnetic field and a high frequency magnetic field, respectively. The high frequency magnetic field is applied to the subject 103 through the transmitter/receiver coil 107. A nuclear magnetic resonance signal generated from the subject 103 is received by the transmitter/receiver coil 107 and is detected by the receiver 108. A nuclear magnetic resonance frequency (detection reference frequency f0) that is a reference of the detection is set by the sequencer 104. The detected signal is transmitted to the calculator 109, where signal processing such as image reconstruction is executed. The result is displayed on the display 110. Optionally, the detected signal or measurement conditions may be stored in the storage medium 111.

Typically, the sequencer 104 performs a control such that each of the devices operates at a timing and an intensity that are programmed in advance. In particular, a program that specifically indicates a high frequency magnetic field, a gradient magnetic field, a signal reception timing, or an intensity is called "pulse sequence (imaging sequence)".

The calculator 109 includes a CPU and a memory, functions as a controller that causes each of the sections in the measurement unit to operate according to the pulse sequence, and functions as an arithmetic device that executes various kinds of signal processing on an echo signal obtained by imaging to obtain a desired image. Although not illustrated in the drawing, the calculator 109 includes an input device for allowing a user to input a setting of imaging conditions.

In order to implement these functions, as illustrated in FIG. 2, the calculator 109 according to the embodiment includes: an image reconstruction unit 220 that obtains a reconstructed image from the measured echo signal; an image arithmetic unit 230 that generates a calculated image or the like using the reconstructed image generated by the image reconstruction unit 210; and a controller 210 that performs an overall control of the devices including the measurement unit 150, the image reconstruction unit 220, and the image arithmetic unit 230.

The image arithmetic unit 230 calculates a quantitative value using, for example, the reconstructed image and a signal function to obtain a quantitative value distribution, that is, an image in which the quantitative value is a pixel value, the signal function being determined by the imaging sequence that is used to obtain the reconstructed image. The quantitative value is at least one of a parameter depending on the subject (subject parameter) or a parameter unique to the device (device parameter) among parameters that determine the signal value.

Specific examples of the subject parameter include a longitudinal relaxation time (T1), a transverse relaxation time (T2), a spin density ($\rho$, a resonance frequency difference ($\Delta f0$), and a diffusion coefficient (D). The resonance frequency difference $\Delta f0$ is a difference between a resonance frequency of each pixel and the reference frequency f0. Examples of the device parameter include a static magnetic field intensity (B0), an irradiation intensity distribution (B1) of a high frequency magnetic field, and a sensitivity distribution (Sc) of a receiver coil. The irradiation intensity distribution B1 and the sensitivity distribution Sc are parameters that depend on not only the device but also the subject.

Examples of the parameters that determine the signal value (pixel value) of the reconstructed image include not only the subject parameter and the device parameter but also an imaging parameter as a parameter that can be arbitrarily set by the user. Examples of the imaging parameter include a repetition time (TR), an echo time (TE), a set intensity of a high frequency magnetic field (flip angle (FA)), and a phase of a high frequency magnetic field ($\theta$).

The signal function is a function representing a relationship between the parameters and the signal value and, once the imaging sequence is determined, can be analytically obtained. In addition, as disclosed in PTL 1, the signal function can also be obtained by numerical simulation. In the embodiment, a case where the signal function is obtained by numerical simulation will be described. Therefore, the image arithmetic unit 230 have functions as: a signal function generating unit 231 that generates a signal function per imaging sequence by numerical simulation; a parameter estimation unit 232 that estimates a subject parameter per pixel using the signal function generated by the signal function generating unit 231 to obtain a subject parameter distribution; and a calculation image generating unit 233 that generates a desired image of the subject from the obtained subject parameter distribution.

Each of the functions implemented by the calculator 109 is implemented by the CPU of the calculator 109 loading a program stored in the storage medium 111 to the memory and executing the loaded program. In addition, some of the functions may be implemented by hardware such as PLC (programmable logic device). The signal function generating unit 231, the parameter estimation unit 232, and the calculation image generating unit 233 may be implemented by a calculator (arithmetic device) that is provided separately from the MRI device 100 and can exchange data with the calculator 109 of the MRI device 100.

Hereinafter, the flow of imaging for obtaining the subject parameter distribution will be described with reference to FIG. 3 by using a case where an imaging target is the head of the subject as an example.

In a case where an imaging sequence is selected or a setting of imaging conditions is received by the user through the input device or the like, the controller 210 transmits an instruction to the sequencer 104 (S301). In the case of imaging for obtaining the parameter distribution, assuming that a combination of plural imaging parameters is a parameter set, plural parameter sets that are different from each other in at least one of the imaging parameters are set. The parameter sets may be preset plural combinations or can be arbitrarily changed or selected by the user. The controller 210 receives a setting of a field of view from the user (S302). In the embodiment, as illustrated in FIG. 4, a field of view 410 is set to include a region of the head 400 from a basilar portion 404 to a vertex portion 405. In a case where a region of interest is not present at the basilar portion, it is not necessary that the field of view includes up to the basilar portion.

The sequencer 104 controls the respective sections of the measurement unit 150 such that imaging is performed under the set imaging conditions (parameter sets). The measurement unit 150 measures an echo signal according to the set imaging sequence and arranges the measured echo signal in a k space (S303).

FIG. 5 illustrates an example of the imaging sequence used to obtain the parameter distribution. In the drawing, RF, A/D, Gs, Gp, and Gr represent a high frequency magnetic field, signal reception, a slice gradient magnetic field, a phase encoding gradient magnetic field, and a readout gradient magnetic field, respectively. This imaging sequence is a RF-spoiled GE sequence, and a pixel value of an image obtained from this imaging sequence mainly depends on the subject parameters T1 and T2* (apparent transverse relaxation time) and the device parameters B1 and Sc.

In this pulse sequence, first, a high frequency magnetic field (RF) pulse 502 is irradiated along with application of a slice gradient magnetic field pulse 501 such that slice magnetization in the target is excited. Next, a slice encoding gradient magnetic field pulse 503 for providing position information in a slice direction and for rephasing, a phase encoding gradient magnetic field pulse 504 for providing position information in a phase encoding direction to a magnetization phase, and a readout gradient magnetic field 505 for dephasing are applied. Next, while applying a readout gradient magnetic field pulse 506 for providing position information in a readout direction, a magnetic resonance signal (gradient echo) is measured during a signal reception time 507. Finally, a phase encoding gradient magnetic field pulse 508 for dephasing and a slice gradient magnetic field pulse 509 for dephasing are applied.

Here, as the RF pulse 502, a RF pulse in which an excitation profile has a specific shape is used in consideration of a relationship with the field of view set in Step S302. FIG. 4 illustrates the relationship between an excitation profile 450 and the field of view 410. In the graph illustrating the profile in the drawing, the horizontal axis represents a position, and the vertical axis represents an excitation intensity. As illustrated in the drawing, the excitation profile 410 has a shape in which it decreases substantially symmetrically before and after a peak.

In the field of view 410, assuming that a body axis direction of the subject is a z direction and a front-rear direction is a y direction, in the example illustrated in the drawing, a slice direction is the z direction, on end portion of the field of view in the z direction substantially matches with the basilar portion 404, and another end portion of the field of view in the z direction is set to be slightly outside of the vertex portion 405. With respect to the field of view that is set as described above, the excitation profile 450 has a peak at the vertex portion 405 and is substantially zero at the basilar portion 404. The relationship between the excitation profile 450 and the field of view 410 is not limited to the example of FIG. 4 as long as it is substantially zero in the vicinity of the basilar portion and has a peak in the vicinity of the vertex portion, and may be adjusted in consideration of aliasing artifact or the like. In addition, in a case where a region of interest is not present at the basilar portion, it is not necessary that the field of view includes up to the basilar portion.

This excitation profile can be implemented using a high frequency magnetic field pulse in which the waveform (intensity) and the phase are adjusted.

First, the waveform of the RF pulse 502 is determined such that a frequency band is narrow, for example, 1 kHz or lower. Specifically, the waveform of the RF pulse 502 has a shape in which it decreases substantially symmetrically and gently on opposite sides of the peak. The peak position of the excitation profile can be shifted to an end portion of the field of view by being shifted by a predetermined phase with respect to a typical RF pulse at the center of the field of view. In order to shift the peak to the vicinity of the end portion of the field of view, it is preferable that the peak position is shifted by a range from about ½ of a full width at half maximum of the excitation profile to the full width at half maximum of the excitation profile. In this case, the shift amount of the phase is in a range of about 90 degrees to 180 degrees during a period from start to end of the application of the RF pulse. The width of the field of view is determined depending on the application time (irradiation time) of the RF pulse and the intensity of the gradient magnetic field that is applied at the same time as the RF pulse is applied. Therefore, once the shape and phase of the RF pulse are set, the above-described excitation profile can be implemented with respect to the set field of view.

In order to shift the peak of the excitation profile to the vicinity of the end portion of the field of view, the center frequency may be shifted instead of the phase of the RF pulse.

The RF pulse having a narrow frequency band that provides a predetermined excitation profile can be stored in advance in the storage unit (the memory or the storage medium 111). When the imaging conditions or the field of view is set, the controller 230 reads the RF pulse from the storage unit and set the read RF pulse to the sequencer 104. Specific examples of the RF pulse having a narrow frequency band and a method of obtaining the same will be described below in detail.

Under the control of the RF pulse by the controller 210, the measurement unit 150 repeats the above-described procedure for the repetition time TR to measure the echo signal multiple times. Per repetition, the intensities (phase encoding amounts kp) of the phase encoding gradient magnetic field pulses (504, 508) and the intensities (slice encoding amounts ks) of the slice encoding gradient magnetic field pulses (503, 509) are changed, and an increased value in the phase of the RF pulse is changed by $\theta_0$ (the phase of the n-th RF pulse is $\theta(n)=\theta(n-1)+\theta_0 \times n$). Each echo signal is arranged on a three-dimensional k space.

The measurement unit 150 repeats the above-described measurement of the echo signal until a number of times of measurement corresponding to a predetermined number of parameter sets ends while changing the parameter set. As a result, the same number of k space data as the number of parameter sets is obtained (S304).

The image reconstruction unit 220 reconstructs images by three-dimensional inverse Fourier-transformation of the collected k space data (S305). Here, the same number of reconstructed images as the number of parameter sets can be obtained.

On the other hand, the signal function generating unit 231 generates the signal function in advance by numerical simulation (S308). The parameter estimation unit 232 estimates the subject parameters using the signal function generated by the signal function generating unit 231 and the plural images generated by the image reconstruction unit 220. The parameter estimation unit 232 calculates the value of the subject parameters (for example, T1 and T2) per pixel and generates a parameter distribution, that is, a parameter image (S306). The parameter image may be displayed on the display 110 as it is, and may be further synthesized with a proton density image by the calculation image generating unit 233 to generate a calculated image such as a weighted image and then displayed on the display 110 (S307).

Methods of the generation of the signal function (S308) and the parameter estimation (S306) are the same as those disclosed in PTL 1. Hereinafter, the flow of the generation of the signal function using the signal function generating unit 231 and the flow of the parameter estimation using the parameter estimation unit 232 will be described with reference to FIG. 6. Here, a case of estimating the subject parameters, T1, T2*, and B1 and the product a (ρSc) of ρ and the device parameter Sc will be described.

First, a signal function 602 is generated in advance by numerical simulation (601). Assuming that FA (flip angle), TR (repetition time), TE (echo time), and θ (RF phase increased value) are provided as the imaging parameters, a signal function fs representing the signal intensity of each pixel is expressed as follows.

[Expression 1]

$$I = fs(\rho, T1, T2, B1, FA, TR, TE, \theta, Sc) \quad (1)$$
$$= \rho Sc \, \exp(-TE/T2) f(T1, T2, B1 \times FA, \theta, TR)$$

In the expression, T1, T2, ρ, B1, and Sc represent the longitudinal relaxation time, the transverse relaxation time, the spin density, the irradiation intensity of RF, and the sensitivity of the receiver coil as the subject parameters, respectively. In a case where an echo signal obtained in imaging is a gradient echo illustrated in FIG. 5, the transverse relaxation time T2 becomes the apparent transverse relaxation time T2*. Whether T2 or T2* is obtained depends on the imaging sequence and is not affected by the parameter estimation method. Therefore, the transverse relaxation time and the apparent transverse relaxation time will be expressed as T2 without being distinguished from each other.

Here, in the signal function fs, B1 functions as a coefficient of FA during imaging, and thus is converted into the form of the product of B1 and FA. In addition, ρ and Sc function as proportionality coefficients on the signal intensity, and thus are on the outside of the function. TE is also applied to the signal intensity in the form of an exponential function, and thus is on the outside of the function.

The imaging parameters FA, TR, and θ are comprehensively changed with respect to arbitrary values of T1 and T2 of the subject parameters. As a result, the signal is generated by numerical simulation, and the signal function is generated by interpolation. The spin density ρ, B1, and Sc of the imaging target are fixed (for example, are fixed to 1).

Ranges where the imaging parameters and the subject parameters are comprehensively changed are set to be included in ranges of the imaging parameters used for actual imaging and ranges of T1 and T2 of the subject. An example of the ranges and values of the parameters to be changed will be shown below.

TR—4 pieces: 10, 20, 30, 40 [ms]
FA 10 values: 5, 10, 15, 20, 25, 30, 35, 40, 50, 60 [degree(s)]
θ—17 pieces: 0, 1, 2, 3, 4, 5, 6, 7, 8, 9, 10, 12, 14, 16, 18, 20, 22 [degree(s)]
T2—17 pieces: 0.01, 0.02, 0.03, 0.04, 0.05, 0.07, 0.1, 0.14, 0.19, 0.27, 0.38, 0.53, 0.74, 1.0, 1.4, 2.0, 2.8 [s]
T1—15 pieces: 0.05, 0.07, 0.1, 0.14, 0.19, 0.27, 0.38, 0.53, 0.74, 1.0, 1.5, 2.0, 2.8, 4.0, 5.6 [s]

In the above-described example, 173400 imaging parameter sets (603) are generated from all the combinations of the imaging parameters and the subject parameters. Regarding these imaging parameter sets, each of signal values is calculated by computer simulation (601).

In the numerical simulation, a subject model in which spins are arranged on lattice points, the imaging sequence, the imaging parameters, and the device parameters are input, and a Block equation that is a fundamental equation of a magnetic resonance phenomenon is solved to output a magnetic resonance signal. The subject model is provided as a spatial distribution of spins (γ, M0, T1, and T2). Here, γ represents a gyromagnetic ratio, and M0 represents a thermal equilibrium magnetization (spin density). By reconstructing an image from the magnetic resonance signal, an image can be obtained under the provided conditions.

The Bloch equation is a first order linear differential equation and is expressed by the following Expression (2).

[Expression 2]

$$\frac{d}{dt}\begin{pmatrix} M_x \\ M_y \\ M_z \end{pmatrix} = \begin{pmatrix} -1/T2 & \gamma H & \\ -\gamma H & -1/T2 & \gamma H1 \\ & -\gamma H1 & -1/T1 \end{pmatrix}\begin{pmatrix} M_x \\ M_y \\ M_z \end{pmatrix} + \begin{pmatrix} 0 \\ 0 \\ M0/T1 \end{pmatrix} \quad (2)$$

$$H = B_0 + G_x x + G_y y + G_z z + 2\pi \Delta f_0/\gamma$$

Here, (x, y, and z) represents a three-dimensional rectangular coordinate system, and z is equal to a direction of a static magnetic field (the intensity is B0). In addition, (Mx, My, and Mz) represents a spin, Gx, Gy, and Gz represent gradient magnetic field intensities in directions indicated by subscripts, respectively, H1 represents a high frequency magnetic field intensity, and Δf0 represents a frequency of a rotary coordinate system.

Based on a signal value obtained from computer simulation, a signal function fs (602) is obtained by interpolation. As the interpolation, first to third linear interpolation or spline interpolation can be used.

FIG. 7 illustrates some intensities in the signal function generated as described above. In this drawing in which the horizontal axis and the vertical axis represent FA and TR, respectively, a case where T1=900 ms, T2=100 ms, and θ=5 degrees is illustrated.

Next, using the signal function fs generated as described above and the plural images obtained in the multiple times of imaging 605, at least one of the subject parameters and the device parameters is estimated (606). In the imaging 605, plural parameter sets that are combinations (parameter sets 604) of the imaging parameters FA, TR and θ and are different from each other in at least one parameter value are used.

FIG. 8 illustrates an example of parameter sets P1 to P6. The imaging parameter sets P1 to P6 are combinations of FA: 10 degrees and 40 degrees, phase increased value θ: 2 degrees, 5 degrees, 7 degrees, 8 degrees, and 22 degrees, and repetition time TR: 10 ms, 30 ms, and 40 ms. In addition, all the values of the gradient echo are 2 ms. This imaging sequence is a RF-spoiled GE sequence illustrated in FIG. 5.

The number of parameter sets is not limited to the above-described example as long as it is more than the number of the values of the subject parameters and the device parameters that is unknown. As the number of parameter sets (number of images) increases, the estimation accuracy is improved. Accordingly, the imaging time increases.

Imaging is performed using the above-described six parameter sets, and T1, T2, B1, and a are estimated (606) using the obtained images (gradient echo images) and the signal function 602 calculated by the numerical simulation 601. Specifically, a signal value I of each pixel is fitted to a function f of the following Expression (3) transformed from Expression (1) to estimate the parameter values as described above.

[Expression 3]

$$I = a \, \exp(-TE/T2) f(T1, T2, \theta, B1 \times FA, TR) \quad (3)$$
$$a = \rho S_e$$

The function fitting can be performed using a least-squares method represented by the following Expression (4).

[Expression 4]

$$\chi^2 = \sum_{FA, \Delta\theta, TR} \{I(FA, \theta, TR, TE) - \quad (4)$$
$$a \, \exp(-TE/T2) f(T1, T2, \theta, B1 \times FA, TR)\} = \min$$

Here, $\chi$ represents the sum of residuals of pixel values of a signal function and a phantom, and I represents a pixel value of an image in a predetermined parameter set (FA, $\theta$, TR, and TE).

By performing the above-described estimation on the signal value (pixel value) of each pixel, a parameter map (parameter image) is obtained.

According to the embodiment, by using the high frequency magnetic field pulse having a narrow frequency band that provides the excitation profile in which it increases (decreases) substantially monotonously in the field of view, the signal value decreases along a blood flow direction, and a change in the estimated value of T1 can be prevented. In addition, by using the high frequency magnetic field pulse having a narrow frequency band, the magnetization transfer effect can be suppressed, and the estimation accuracy of T1 and T2 can be improved. The embodiment is suitable particularly for imaging for generating a calculated image of the head, and by setting an end portion of the field of view to be in the vicinity of the vertex portion, the problem of aliasing caused by excitation outside of the field of view can be avoided without using a specific aliasing removal unit.

In the embodiment, the relationship between the shape and excitation profile of the RF pulse for excitation included in the imaging sequence and the field of view has been described. Hereinafter, specific examples of the RF pulse and excitation profiles thereof will be described by using head imaging as an example.

Example 1 of RF Pulse

In this example, as the RF pulse (FIG. 5: 502) for excitation, only a main lobe (one peak) of a sinc function is used, and the application time is set as 2.4 ms. FIG. 9A illustrates the intensity and the phase. In addition, FIG. 9B illustrates an excitation profile 451 of the RF pulse.

Assuming that the application time is represented by t sec and the number of peaks is represented by n, a frequency band (full width at half maximum) of a sinc function is approximately represented by (n+1)/t Hz. Since the application time is 2.4 ms and the number of peaks is 1 in this excitation pulse, the frequency band (full width at half maximum) is 0.83 kHz. In a case where the frequency band is 1 kHz or lower, the magnetization transfer effect can be suppressed. Therefore, by using the excitation pulse of FIGS. 9A-9B, a subject parameter distribution can be obtained substantially without being affected by magnetization transfer.

In an excitation pulse of the related art, for example, a sinc function shape having nine peaks is used in order to cause excitation to uniformly occur in a field of view and to make an excitation profile thereof zero on the outside of the field of view. In a case where the application time is set as 2.4 ms as in the case of the example, the frequency band is 4.2 kHz, and the magnetization transfer effect is extremely high.

FIG. 10 illustrates a variation in the T1 value of brain white matter depending on the frequency band of the high frequency magnetic field pulse for excitation. This T1 value is a value obtained by actually imaging the head of a volunteer using the pulse sequence of FIG. 5. As can be seen from FIG. 10, the calculated T1 value largely depends on the frequency band. In a case where the frequency band is 1 kHz or lower (0.84 kHz), the obtained value is close to literature data (about 750 ms to 1084 ms) of the T1 value of brain white matter. However, in a case where the frequency band is 2.5 kHz or higher, the obtained value is largely shifted from literature data. The reason for this is presumed to be as follows. As the frequency band increases, the magnetization transfer effect increases. Therefore, as compared to a case where the magnetization transfer effect is low under imaging conditions where FA is high, the signal value decreases, and the T1 value is calculated to be high.

On the other hand, as illustrated in FIG. 9B, a field of view 451 is set to be substantially the same as a range from the vicinity of the basilar portion 404 to the vicinity of the vertex portion 405, and an excitation profile 411 is adjusted with respect to the field of view such that a peak is on the side of a field-of-view end portion. That is, the intensity of the excitation profile 451 is substantially zero in a direction from the vicinity of the basilar portion 404 to the neck and increases gently toward the vertex portion 405. After the intensity reaches the maximum (peak) in the vicinity of the vertex portion, the intensity gradually decreases and becomes zero in the end. Accordingly, as in the case of MR angiography of the related art, the flip angle is small at the basilar portion and increases toward the vertex portion. Therefore, the blood signal can be made to be substantially uniform, and a subject parameter distribution of blood can be accurately obtained without depending on regions.

In addition, since the z direction is a slice encoding direction, there is a problem of aliasing artifact in a signal at an end portion in the z direction. The excitation profile 451 illustrated in FIG. 9B is substantially zero in the direction from the vicinity of the basilar portion 404 to the neck. Therefore, aliasing does not occur toward the vertex portion 405. In addition, a target that generates a signal is not present after the vertex portion. Therefore, even in a case where the excitation profile is not zero, there is no problem of aliasing.

Example 2 of RF Pulse

In this example, as the RF pulse (FIG. 5: 502) for excitation, a gaussian function is used. The application time is set as 4.8 ms. FIG. 11A illustrates the intensity and the phase. In addition, FIG. 11B illustrates a positional relationship between an excitation profile 452 of the RF pulse and a field of view 412.

Under the same application time, the frequency band of the excitation pulse having a gaussian function shape is about two times that of the sinc function having one peak. In FIG. 11B, the application time of the RF pulse is two times that of the sinc function of Example 1 (FIG. 9A). Therefore, the frequency band is about 0.8 kHz which is substantially the same as that of the RF pulse of FIG. 9A. Accordingly, even in a case where this excitation pulse is used, a subject parameter distribution can be obtained in a state where there is substantially no magnetization transfer effect.

In addition, as illustrated in FIG. 11B, a field of view in the z direction is set to be substantially the same as a range from the vicinity of the basilar portion 404 to the vicinity of the vertex portion 405. The excitation profile 452 is substantially zero in a direction from the vicinity of the basilar portion 404 to the neck and increases gently toward the vertex portion. After the excitation profile 452 reaches the maximum (peak) in the vicinity of the vertex portion 405, the excitation profile 452 gradually decreases and becomes zero in the end. Accordingly, as in the case of MR angiography of the related art, the flip angle is small at the basilar portion and increases toward the vertex portion. Therefore, the blood signal can be made to be substantially uniform, and a subject parameter distribution of blood can be obtained without depending on regions.

Example 3

In Examples 1 and 2, the excitation profile having the known function or a processed shape thereof is used. However, in this example, a RF pulse having a narrow frequency band that provides an excitation profile having a shape similar to a desired excitation profile is designed from the desired excitation profile.

A method of designing the excitation pulse will be described using FIGS. 12A-12D. FIG. 12A illustrates a desired excitation profile having a shape, for example, an isosceles triangle in which the intensity decreases symmetrically with respect to the apex at the center. By Fourier-transformation of the excitation profile, a pulse shape in which the horizontal axis represents the time is obtained as illustrated in FIG. 12B. In this pulse shape, side lobes are generated on the right and left sides of a main lobe.

FIG. 12C illustrating a waveform obtained by cutting out only the main lobe from the waveform. By cutting out only the main lobe, the frequency band can be set to be narrower than that of the waveform including the side lobes of the application time. In a case where the application time is 2.4 ms, the frequency band of the waveform is about 0.8 kHz which is the same as that of the sinc function having one peak. Accordingly, even with this excitation pulse, the magnetization transfer effect can be substantially suppressed.

In a case where a phase of the waveform (RF pulse waveform) illustrated in FIG. 12C is modulated into a linear form as illustrated on the left side of FIG. 12C and undergoes inverse Fourier-transformation, an excitation profile 453 illustrated in FIG. 12D is obtained. By modulating the phase as described above, the peak position can be slightly shifted to the right side from the center, and the peak position can be positioned in the vicinity of the vertex portion. The peak position can also shifted by offsetting the frequency of the RF pulse from the center frequency as described above. The peak position shift amount Δz has a relationship of Δz=Δf/(γGs) in which Δf represents the frequency offset amount and Gs represents the slice gradient magnetic field intensity. Here, γ represents the gyromagnetic ratio. According to this relational expression, the frequency offset amount is adjusted such that the peak position is in the vicinity of the vertex portion.

FIG. 13 illustrates a positional relationship between the excitation profile 453 of the RF pulse according to the example and a field of view 413. Even in the example, the excitation profile 453 is substantially zero in the vicinity of the basilar portion 404 and increases gently toward the vertex portion 405. After the excitation profile 453 reaches the maximum (peak) at the vertex portion 405, the excitation profile 453 gradually decreases and becomes zero in the end.

In addition, in the example, the field of view is set to be in a range from a region that is slightly closer to the neck than the vicinity of the basilar portion 404 to the vicinity of the vertex portion 405, and aliasing artifact can be prevented. That is, in a case where imaging is performed such that the field of view does not include a portion 453a where the excitation profile slightly protrudes from the vicinity of the basilar portion 404, a signal that is generated from a spin excited in this portion appears to overlap the vertex portion as aliasing artifact. However, by allowing the field of view to include the protruded portion 453a, the occurrence of aliasing artifact can be prevented.

Aliasing artifact can also be suppressed by widening the field of view up to a region slightly above the vicinity of the vertex portion 405 as illustrated in FIG. 9B or 11B. Even in this case, the protruded portion in the vicinity of the basilar portion 404 wraps around the vertex portion side of the field of view. However, aliasing occurs in a region of the widened field of view in the vicinity of the vertex portion, and thus causes no problem without overlapping the head.

Example 4

This example is the same as the example 3 in that, by designating a desired excitation profile, an excitation pulse having a narrow frequency band that provides an excitation profile having a shape similar to the desired excitation profile is designed. In this example, as the desired excitation profile, an excitation profile having an asymmetric shape is used.

The excitation profile designated in the example has a shape 143 in which, as illustrated in FIG. 14A, it rises slightly rapidly at a portion 141 positioned at the basilar portion, reaches the peak at a portion 142 positioned at the vertex portion, and then gradually decreases toward zero. By Fourier-transformation of the excitation profile, a shape in which side lobes are generated on the right and left sides of a main lobe is obtained as illustrated in FIG. 14B.

By cutting out only the main lobe from this waveform, a waveform illustrated in FIG. 14C is obtained. The left sides of FIGS. 14B and 14C illustrate phases of the respective waveforms. By cutting out only the main lobe, the frequency band can be set to be narrower than that of the waveform including the side lobes of the application time. Specifically, in a case where the application time is 2.4 ms, the frequency band of the waveform is about 0.8 kHz which is the same as that of the sinc function having one peak. Accordingly, even with this excitation pulse, the magnetization transfer effect can be substantially suppressed.

By inverse Fourier-transformation of the waveform illustrated in FIG. 14C, an excitation profile 454 illustrated in FIG. 14D is obtained. The shape of the example has a peak at a position where the designated excitation profile is biased toward the z direction. Therefore, the phase is already modulated in the step of FIG. 14B. Accordingly, it is not necessary to additionally modulate the phase as in the case of Example 3 In the shape of the excitation profile 454, the frequency band is narrowed by cutting off the side lobes from the pulse waveform. Therefore, the shape is smoother than the original shape.

In addition, as illustrated in FIG. 15, an excitation profile 454 of this example is substantially zero in the vicinity of the basilar portion 404 and increases gently toward the vertex portion 405. After the excitation profile 454 reaches the maximum (peak) in the vicinity of the vertex portion 405, the excitation profile 454 gradually decreases and becomes zero in the end in a state where the side lobes remain. In the example, a subject parameter distribution is obtained with a high SN ratio until the basilar portion 404. The excitation profile becomes completely zero at a position slightly below the vicinity of the basilar portion such that a signal of the basilar portion is prevented from becoming zero.

In this case, aliasing of a portion where the excitation profile slightly protrudes from the vicinity of the basilar portion 404 appears in the field of view on the vertex side. In order to prevent overlapping with the vertex as much as possible, a field of view 414 in the z direction is set to be in a range from the vicinity of the basilar portion 404 to a region slightly above the vicinity of the vertex portion 405.

FIG. 16A illustrates a B1 map (FA map) on a coronal plane in a case where an adult human head portion is imaged under the conditions of the example. FIG. 16B illustrates a profile in a line L illustrated in FIG. 16A. As illustrated in FIG. 16B, the FA profile has a peak in the vicinity of the vertex (in the vicinity of an end portion of a brain 401) and decreases toward the basilar portion. A portion (portion 403 surrounded by O) where the intensity slightly rises at a skin 402 in the vicinity of the end portion of the vertex is present because of aliasing of an end portion of the basilar portion protruding from the field of view.

Hereinabove, the examples of the Rf pulse for excitation to be used in the imaging sequence for the parameter estimation according to the embodiment have been described. The RF pulse for excitation is not limited to the examples as long as the frequency band is narrow, for example, 1 kHz or lower and the excitation profile has a peak on one end portion side and monotonously decreases substantially symmetrically on opposite sides of the peak regarding the relationship with the field of view.

In addition, in the above description of the embodiment, the present invention is applied to the MRI device. As illustrated in FIG. 17, the function of the image arithmetic unit 230 of the MRI device 100 can also be implemented by a separate arithmetic device 300 from the MRI device 100, and a system including the MRI device 100 and the arithmetic device 300 is also included in the present invention. The arithmetic device 300 implements the function of the parameter estimation unit 232. In addition to the parameter estimation unit 232, the signal function generating unit 231 may be further provided. Further, in a case where the RF pulse is designed from the designated excitation profile as in the case of Examples 3 and 4, a function as an RF pulse calculation unit 235 that receives the desired excitation profile and calculates the RF pulse may be added.

In this system, in order to exchange data between the MRI device 100 and the arithmetic device 300, well-known unit such as wired or wireless data transfer unit or a portable medium can be adopted. In addition, the arithmetic device 300 may be constructed by cloud computing or the like, or may be constructed using plural CPUs. By implementing the predetermined arithmetic function using a separate modality from the MRI device, the degree of freedom of the user increases, and a load on the calculator in the MRI device can be reduced.

REFERENCE SIGNS LIST

100: MRI device
m101: magnet that generates static magnetic field
102: gradient magnetic field coil
103: subject
104: sequencer
105: gradient magnetic field power supply
106: high frequency magnetic field generator
107: probe
108: receiver
109: calculator
110: display
111: storage medium
210: controller
220: image reconstruction unit
230: image arithmetic unit
231: signal function generating unit
232: parameter estimation unit
233: calculation image generating unit
235: RF pulse calculation unit
300: arithmetic device
400: imaging target
404: basilar portion
405: vertex portion
410: field of view
411: field of view
412: field of view
413: field of view
414: field of view
450: excitation profile
451: excitation profile
452: excitation profile
453: excitation profile
454: excitation profile

The invention claimed is:

1. A magnetic resonance imaging device comprising:
a measurement unit that applies a high frequency magnetic field and a gradient magnetic field to a subject placed in a static magnetic field according to a predetermined imaging sequence to measure an echo signal generated from the subject;
an image reconstruction unit that obtains a reconstructed image from the measured echo signal; and
a parameter estimation unit that estimates a quantitative value distribution of the subject using a plurality of reconstructed images and a signal function, the reconstructed images being obtained by performing imaging multiple times under different imaging conditions of the imaging sequence, and the signal function determining a relationship between a quantitative value of the subject or a device and a signal value of each of the reconstructed images, wherein
the measurement unit uses, as a high frequency magnetic field pulse for excitation to be used in the imaging sequence, a high frequency magnetic field pulse that has a peak in the vicinity of one end portion of a field of view and provides an excitation profile having a shape in which the excitation profile decreases almost symmetrically on opposite sides of the peak.

2. The magnetic resonance imaging device according to claim 1, wherein
the high frequency magnetic field pulse has a frequency band of 1 kHz or less.

3. The magnetic resonance imaging device according to claim 1, wherein
a waveform of the high frequency magnetic field pulse is a Gaussian function or a main lobe of a sinc function.

4. The magnetic resonance imaging device according to claim 1, wherein
a waveform of the high frequency magnetic field pulse is obtained by cutting out only a main lobe from a waveform that is obtained by Fourier-transformation of a preset excitation profile.

5. The magnetic resonance imaging device according to claim 1, wherein
the excitation profile of the high frequency magnetic field pulse has a one-dimensional shape in a body axis direction of the subject.

6. The magnetic resonance imaging device according to claim 5, wherein
the field of view includes a region from a basilar portion to a vertex portion of the subject, and
the excitation profile is zero at the basilar portion, at a field-of-view end portion that is closest to the basilar portion, or at a portion between the field-of-view end portion and the basilar portion.

7. The magnetic resonance imaging device according to claim 5, wherein
the field of view includes a region from a basilar portion to a vertex portion of the subject, and
a peak position of the excitation profile is positioned at the vertex portion, at a field-of-view end portion that is closest to the vertex portion, or at a portion between the field-of-view end portion and the vertex portion.

8. The magnetic resonance imaging device according to claim 7, wherein
the excitation profile is zero at the basilar portion, at a field-of-view end portion that is closest to the basilar portion, or at a portion between the field-of-view end portion and the basilar portion.

9. A magnetic resonance imaging system comprising:
a magnetic resonance imaging device including a measurement unit that applies a high frequency magnetic field and a gradient magnetic field to a subject placed in a static magnetic field according to a predetermined imaging sequence to measure an echo signal generated from the subject, an image reconstruction unit that obtains a reconstructed image from the measured echo signal, and a controller that controls the measurement unit and the image processing unit; and
an arithmetic device that exchanges data with the magnetic resonance imaging device, wherein
the controller performs imaging multiple times under different imaging conditions by using, as a high frequency magnetic field pulse for excitation to be used in the imaging sequence, a high frequency magnetic field pulse that has a peak in the vicinity of one end portion of a field of view and provides an excitation profile having a shape in which the excitation profile decreases almost symmetrically on opposite sides of the peak,
the arithmetic device is programmed to estimate a quantitative value distribution of the subject, and
the arithmetic device is programmed to receive a plurality of reconstructed images from the magnetic resonance imaging device during the multiple times of imaging under the different imaging conditions, and estimate the quantitative value distribution of the subject using the reconstructed images and a signal function that determines a relationship between a quantitative value of the subject or a device and a signal value of each of the reconstructed images.

10. The magnetic resonance imaging system according to claim 9, wherein
the arithmetic device is programmed to calculate the high frequency magnetic field pulse for excitation using a designated excitation profile, the high frequency magnetic field pulse for excitation being used for the imaging of the magnetic resonance imaging device.

11. A magnetic resonance imaging method comprising:
applying a high frequency magnetic field and a gradient magnetic field to a subject placed in a static magnetic field according to a predetermined imagine sequence to measure an echo signal generated from the subject;
obtaining a reconstructed image from the measured image signal;
estimating a quantitative value distribution of a subject using a plurality of reconstructed images and a signal function, the reconstructed images being obtained by performing imaging multiple times under different imaging conditions of the imaging sequence, and the signal function determining a relationship between a quantitative value of the subject or a device and a signal value of each of the reconstructed images, wherein
during the multiple times of imaging, a high frequency magnetic field pulse that has a peak in the vicinity of one end portion of a field of view and provides an excitation profile having a shape in which the excitation profile decreases almost symmetrically on opposite sides of the peak is used as a high frequency magnetic field pulse for excitation.

12. The magnetic resonance imaging method according to claim 11, wherein
an imaging target is a head of the subject, and
the field of view is set such that a vertex portion of the head is in the vicinity of one end portion of the field of view.

* * * * *